(12) United States Patent
Patterson

(10) Patent No.: US 6,379,323 B1
(45) Date of Patent: Apr. 30, 2002

(54) BIO ERODABLE MYRINGOTOMY TUBE

(75) Inventor: Matthew C. Patterson, Minneapolis, MN (US)

(73) Assignee: Acoustic Technologies, Inc., Northfield, MN (US)

(*) Notice: Subject to any disclaimer, the term of this patent is extended or adjusted under 35 U.S.C. 154(b) by 0 days.

(21) Appl. No.: 09/390,229

(22) Filed: Sep. 3, 1999

Related U.S. Application Data

(63) Continuation-in-part of application No. 08/935,666, filed on Sep. 23, 1997, now abandoned, which is a continuation-in-part of application No. 08/853,668, filed on May 9, 1997, now abandoned.

(51) Int. Cl.[7] .............. A61M 5/00; A61F 2/06; A61F 2/18; A61F 11/00
(52) U.S. Cl. ............. 604/8; 623/1.37; 623/1.38; 623/10; 606/109
(58) Field of Search .............. 604/8–10, 264, 604/523, 265; 623/1, 1.1, 1.3, 1.31, 1.37, 1.38, 1.42, 1.45, 1.46, 1.47, 11, 12, 10, 66.1, 924; 606/109

(56) References Cited

U.S. PATENT DOCUMENTS

| | | | |
|---|---|---|---|
| 3,871,380 A | | 3/1975 | Heros |
| 3,897,786 A | | 8/1975 | Garnett et al. |
| 3,948,271 A | * | 4/1976 | Akiyama ............ 128/350 R |
| 4,168,697 A | * | 9/1979 | Cantekin |
| 4,174,716 A | | 11/1979 | Treace |
| 4,326,512 A | * | 4/1982 | Peerless |
| 4,468,218 A | | 8/1984 | Armstrong |
| 4,473,073 A | | 9/1984 | Darnell |
| D276,937 S | | 12/1984 | Griggs |
| 4,650,488 A | * | 3/1987 | Bays et al. |
| 4,695,275 A | * | 9/1987 | Bruce et al. |
| 4,913,132 A | | 4/1990 | Gabriel |
| 5,026,378 A | | 6/1991 | Goldsmith III |
| 5,053,040 A | | 10/1991 | Goldsmith III |
| 5,197,977 A | * | 3/1993 | Hoffman, Jr. et al. |
| 5,254,120 A | | 10/1993 | Cinberg et al. |
| 5,350,580 A | * | 9/1994 | Muchow et al. |
| 5,413,597 A | * | 5/1995 | Krajicek ............ 628/1 |
| 5,421,818 A | | 6/1995 | Arenberg |
| 5,466,239 A | | 11/1995 | Cinberg et al. |
| 5,489,286 A | | 2/1996 | Cinberg et al. |

FOREIGN PATENT DOCUMENTS

| | | |
|---|---|---|
| DE | 27 56 256 A1 | 6/1979 |
| WO | WO 94/13234 | 6/1994 |

* cited by examiner

Primary Examiner—Jeffrey R. Jastrzab
Assistant Examiner—Patricia Bianco
(74) Attorney, Agent, or Firm—Merchant & Gould P.C.

(57) ABSTRACT

A bio erodable myringotomy tube which is bio erodable and does not require removal.

7 Claims, 3 Drawing Sheets

BIO ERODABLE MYRINGOTOMY TUBE

CROSS-REFERENCE TO RELATED APPLICATION

This application is a continuation-in-part of application Ser. No. 08/935,666, filed on Sep. 23, 1997, now abandoned, which in turn is a continuation-in-part of application Ser. No. 08/853,668, filed on May 9, 1997, now abandoned.

BACKGROUND OF THE INVENTION

The present invention relates to the field of otology implants and is particularly directed toward a myringotomy tube.

Since about 1952 myringotomy tubes (also referred to as tympanotomy tubes) have been used as a form of treatment for recurrent infections in the ear and for abnormal pressure and fluid in the middle ear behind the eardrum due to abnormal ventilation of the middle ear. The purpose of any myringotomy tube is to maintain a connection between the external auditory canal and the middle ear space. This allows for ventilation of the middle ear space with air, and for the evacuation of purulent material and fluid from the middle ear space. More than two million operations are performed yearly in the United States wherein these tubes are surgically inserted into the ear drum (tympanic membrane) so as to provide fluid communication between the middle ear and the external canal.

Myringotomy tubes typically stay in the ear drum for four to thirty-six months, depending upon the age of the patient and the shape of the tube. Most patients in the younger age groups (1–6 years) require a myringotomy tube for twelve to twenty-four months. Older patients may require very short term tubes (1–3 months) or long term tubes (2–3 years) depending upon their etiology of their otologic dysfunction.

The ideal myringotomy tube would stay in place indefinitely without extruding, but would instantly be gone from the ear when the patient no longer needed ventilation of the middle ear. Numerous designs have been developed which allow myringotomy tubes to stay in position for long periods (at least 1 year or more) without extruding. Unfortunately, many of these tubes never extrude and must be surgically removed. This removal risks injury to the surrounding ear drum and any middle ear structures which may have connected to the tube by fibrous adhesions in the middle ear. In addition, this procedure must be done under anesthesia on children who do not tolerate such manipulation in the clinic or office setting. Furthermore, myringotomy tubes that do not extrude after twenty-four months very often cause a permanent perforation of the ear drum after they are surgically removed. This perforation must be surgically repaired.

Other myringotomy tubes have been designed to avoid the problem of myringotomy tubes staying in place longer than desired (2–3 years or more). Unfortunately, by the nature of their design, these tubes extrude easily and often extrude during the first four months after placement. This premature extrusion results in recurrent disease and usually results in the myringotomy tube having to be replaced in the ear drum. Again, in children, this requires another operating room procedure.

The present invention solves the problems noted above associated with existing myringotomy tubes.

SUMMARY OF THE INVENTION

The present invention relates to a bioerodable myringotomy tube.

The invention is to be made of various forms of collagen, which is a natural architectural component of the tissues of the human body. Gelatin is a variation of collagen that is prepared and manufactured in various ways. The invention, in its preferred form, is to be made of a form of gelatin called GELFILM®. In other forms, the invention is to be made of other forms of collagen and gelatin, not specifically GELFILM®.

In one embodiment of the present invention, there is provided a myringotomy tube for providing drainage of the middle ear through the external ear canal. The myringotomy tube is comprised of a member having a passageway provided therein for communicating the middle ear with the external ear canal subsequent to the member having been inserted through a surgical incision in the tympanic membrane. The myringotomy tube is further comprised of a bio erodable material so as to dissolve upon exposure to middle ear fluids, whereby the myringotomy tube does not have to be surgically removed from the tympanic membrane.

In one embodiment, the bio erodable material dissolves over a period of nine to twelve months.

In a preferred embodiment, the myringotomy tube is made from GELFILM®. GELFILM® has a long half-life (approximately one year when used in the middle ear).

In still another embodiment, the myringotomy tube might be made of GELFILM® which is impregnated with various broad spectrum antibiotics so as to assist in the treatment of infection or disease in the ear. As the tube dissolves, the antibiotic is released, aiding in the prevention of infections in the middle ear.

In another embodiment, the myringotomy tube might be made of forms of gelatin other than GELFILM®.

In still another embodiment, the myringotomy tube might be made of collagen that is not in the form of a gelatin or GELFILM®.

In still another embodiment, the myringotomy tube might be made of gelatin other than GELFILM® which is impregnated with various broad spectrum antibiotics.

In still another embodiment, the myringotomy tube might be made of collagen that is not in the form of a gelatin or GELFILM® and which is impregnated with various broad spectrum antibiotics.

For a standard, non-dissolvable myringotomy tube, the connection between the middle ear space and the external canal is maintained until such time as the tube dislodges from the tympanic membrane and migrates out of a functional position. On the other hand, for a dissolvable myringotomy tube, additional structural considerations must be taken into account. A dissolvable tube dissolves over a period of time thus causing a potential change to the size and patency of the inner lumen of the tube. As a tube is not functional when the lumen patency is lost, not maintaining the tubes opening becomes a continuous threat to the effectiveness of a dissolvable tube once the tube is exposed to bodily fluids that result in the tube's dissolution.

Applicant has found that as the collagen myringotomy tube dissolves, the shaft tends to lose its lumen patency and collapse upon itself if the internal diameter is not made large enough. Premature collapse of the tube blocks the passageway and prevents proper drainage of the middle ear. Therefore, in yet another embodiment of the invention, the passageway of the shaft has an internal diameter of at least about 2.0 mm. Applicant has discovered that the passageway must have an internal diameter of at least about 2.0 mm in order to prevent premature collapse of the shaft as the collagen dissolves. Passageways with internal diameters less than 2.0 mm tend to collapse upon themselves thereby blocking the passageway and rendering the tube non-functional.

It is a purpose of a preferred embodiment of the present invention, to provide a myringotomy tube which further provides for long term stability in the ear drum, without premature extrusion.

A bio erodable or dissolvable myringotomy tube avoids many of the problems associated with standard non-dissolvable tubes.

These and various other advantages and features of novelty which characterize the invention are pointed out with particularity in the claims annexed hereto and forming a part hereof. However, for a better understanding of the invention, its advantages, and the objects obtained by its use, reference should be made to the accompanying drawings and descriptive matter, which form a further part hereof, and in which there is illustrated and described a preferred embodiment of the invention.

BRIEF DESCRIPTION OF THE DRAWINGS

In the drawings wherein corresponding reference numerals generally indicate corresponding parts throughout the several views.

DETAILED DESCRIPTION OF PREFERRED EMBODIMENT(S)

The drawings provided represent the preferred shape, size, and configuration of the bioerodable myringotomy tube. However, other embodiments of this bioerodable myringotomy tube might be of alternative shapes, sizes, and configurations. These alternative embodiments of the bio-erodable myringotomy tube might include a bevelled design with various angles between the shaft of the tube and the ends, larger or smaller internal and/or external ends, and various shapes and angles of the ends.

Figure 1:
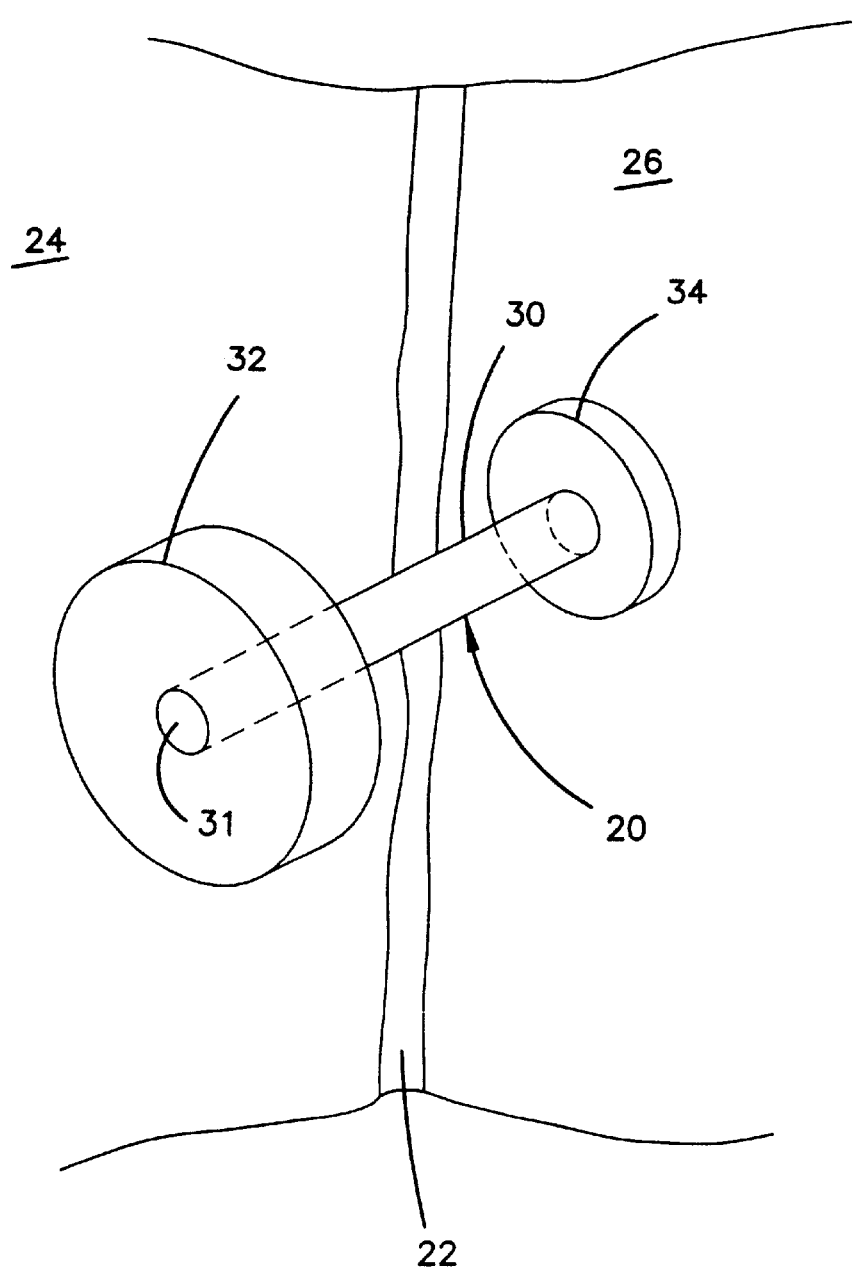
FIG. 1 is a diagrammatic perspective view of a myringotomy tube in accordance with the principles of the present invention disposed in the ear drum.

Referring now to the figures, there is diagramatically illustrated in FIG. 1 an embodiment of a myringotomy tube 20 positioned in an eardrum 22 so as to provide communication between a middle ear 24 and an external ear canal 26.

Figure 2:
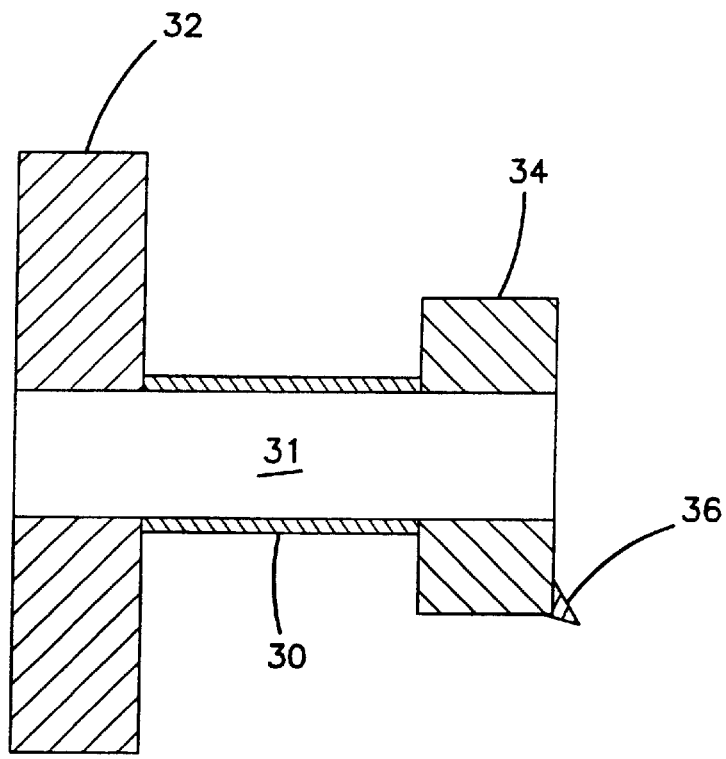
FIG. 2 is a diagrammatic side view of the myringotomy tube shown in FIG. 1.
Figure 3:
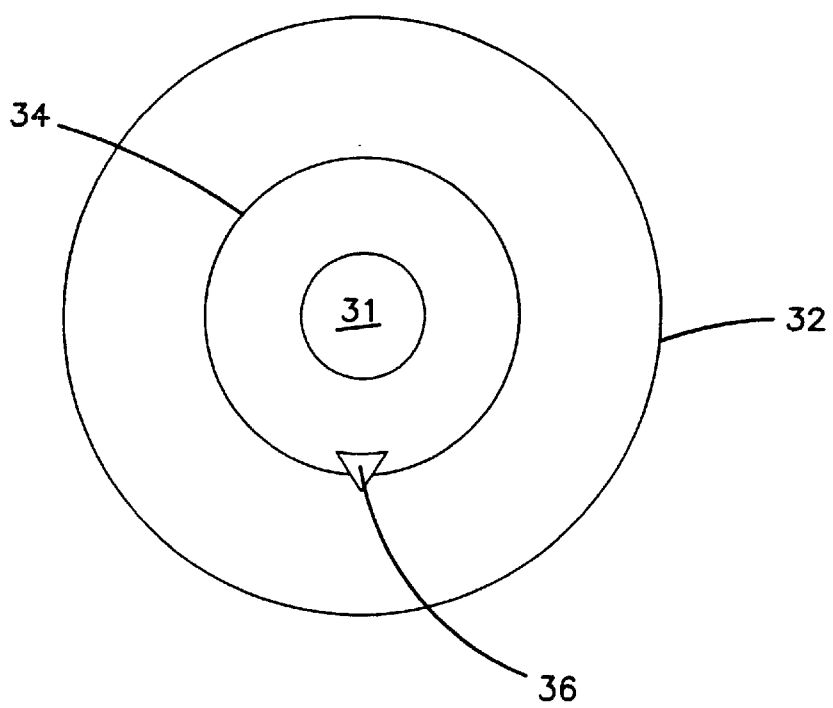
FIG. 3 is an diagrammatic end view of the myringotomy tube shown in FIG. 1.

It will be appreciated that the myringotomy tube 20 might take on varying configurations and still be in keeping with the principles of the present invention. As shown in FIGS. 2 and 3, one embodiment of the myringotomy tube 20 might have a hollow shaft 30 defining a passageway 31 extending from one end 32 to another end 34. The end 32 is disposed in the middle ear 24 and the end 34 is disposed in the external canal 26 upon insertion of the myringotomy tube 20 through a surgical incision in the eardrum 22. Upon insertion of the myringotomy tube 20 into the eardrum 22, fluid communication is provided between the middle ear 24 and the external ear canal 26 whereby fluid can drain from the middle ear 24 to the external canal 26. In the embodiment shown, the end 32 has a diameter of roughly 40 mm and the end 34 has a diameter of 2.4 mm. Disposed on the end 34, is a tab 36 for engagement by a surgical instrument so as to enable insertion through an incision in the ear drum 22.

The passageway 31 has an internal diameter d of sufficient size to prevent the shaft from collapsing upon itself prematurely so as to maintain the lumen patency of the tube 20. If the shaft 30 collapses, the passageway becomes partially or completely blocked, thereby preventing adequate drainage of the middle ear. More particularly, it has been found that the internal diameter d must be at least about 2.0 mm to provide adequate strength to the shaft 30 to prevent it from prematurely collapsing as the material of the myringotomy tube dissolves. Internal diameters less than this value do not provide the shaft with sufficient strength to prevent premature collapse.

As shown in FIGS. 1 and 3, the ends 32,34 are generally circular in shape. However, the ends 32,34 could have shapes other than a circle, such as oval, triangle, rectangle, and oblong.

Figure 4:
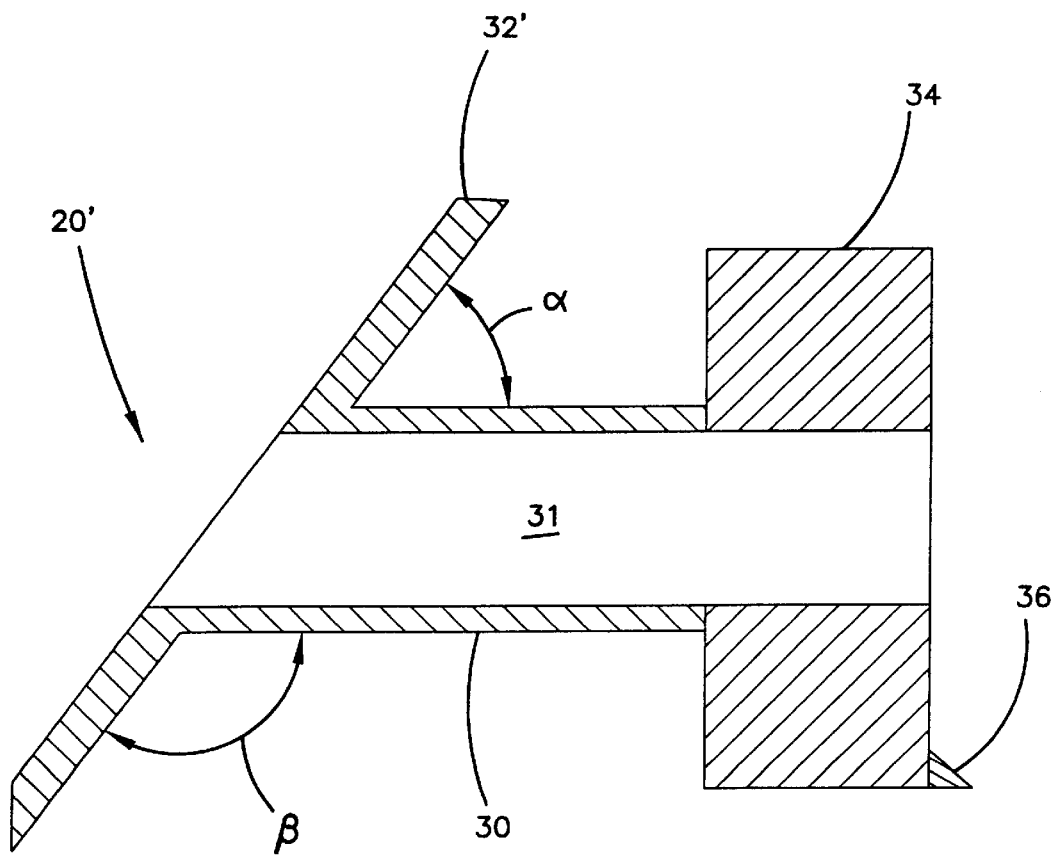
FIG. 4 is a diagrammatic side view of an alternate embodiment of the myringotomy tube.

FIG. 4 illustrates an alternate embodiment of a myringotomy tube 20', in which the end 32' is angled relative to the shaft 30, with the end 34 being the same as in the first embodiment shown in FIG. 2. The end 32' can be angled relative to the longitudinal axis of the shaft such that the angle a is approximately 45 degrees and the angle β is approximately 135 degrees, although smaller or larger angles could be used as well. The tube 20' is otherwise similar to the first embodiment.

In the preferred embodiment of the present invention, the myringotomy tube 20 is made of a material which is bio erodable upon exposure to middle ear fluids. In one embodiment, the myringotomy tube 20 might dissolve in nine to twelve months. Any remaining portions of the tube 20, might then be washed away by use of particular solvents.

An example of such a bio erodable material is GEL-FILM® which is made by The UpJohn Company of Kalamazoo, Mich. GELFILM® is a material that has been used for many years safely in the middle ear. It has been used to provide temporary support to structures that have been surgically repaired and require a scaffolding to maintain a certain position until healing has occurred. The material dissolves in approximately one year and its components; collagen, water and nitrogen are resorbed by the body without sequelae. GELFILM® is also dissolvable in certain solvents. Such solvents could be used to irrigate the external ear, resulting in the dissolution of the myringotomy tube. This would provide a simple and safe method for the removal of GELFILM® myringotomy tubes prior to their natural dissolution, should the physician deem the tube no longer necessary. This avoids the above mentioned risks of physically extracting the myringotomy tube, and in children, alleviates the need for an operating room procedure.

It will be appreciated that the myringotomy tube might be made of any number of different materials dissolvable in middle ear fluids. For example, the myringotomy tube 20 might be made of a collagen, a naturally occurring animal protein. Depending upon the form of collagen used to make each embodiment of the tube (collagen, gelatin or GELFILM®), and depending upon the specific manufacturing process employed to make each embodiment of the tube, the various embodiments of the tube may dissolve in middle ear fluids after anywhere from 3 months to 12 months of exposure to such fluids.

In yet other embodiments, the myringotomy tube 20 might also be impregnated with broad spectrum antibiotics which are released as the myringotomy tube erodes in the body or is dissolved by the application of a solution so as to assist in the treatment of disease or infection of the ear.

It is to be understood, that even though numerous characteristics and advantages of the invention have been set forth in the foregoing description, together with details of the structure and function of the invention, the disclosure is illustrative only, and changes may be made in detail, especially in matters of shape, size, and arrangement of the parts within the principles of the invention to the full extent indicated by the broad general meaning of the terms in which the appended claims are expressed.

What is claimed is:

1. A myringotomy tube insertable into an opening in a tympanic membrane to provide drainage of the middle ear through the external ear canal, the myringotomy tube comprising a shaft adapted for disposition in the opening of the tympanic membrane and having a passageway provided therein extending between first and second ends thereof for communicating the middle ear with the external ear canal when the shaft is inserted in the opening, wherein the passageway has an internal diameter that is at least 2.0 mm, the internal diameter being substantially constant from the first end to the second end, the myringotomy tube further including a first flange on the first end of the shaft and a second flange on the second end of the shaft, the myringotomy tube being sized such that the first flange and the second flange are disposed on opposite sides of the tympanic membrane when the shaft is disposed in the opening such that the first flange is extendable into the middle ear and the second flange is extendable into the external ear canal, and the myringotomy tube being further comprised of a bioerodable material that is dissolvable upon exposure to middle ear fluids, whereby the myringotomy tube does not have to be surgically removed.

2. A myringotomy tube in accordance with claim 1, wherein the myringotomy tube is made from collagen.

3. A myringotomy tube in accordance with claim 2, wherein the collagen is in the form of a gelatin material.

4. A myringotomy tube in accordance with claim 1, wherein the myringotomy tube is impregnated with an antibiotic.

5. A myringotomy tube in accordance with claim 1, wherein said first flange is disposed at an acute angle relative to a longitudinal axis of said shaft.

6. A myringotomy tube in accordance with claim 5, wherein the myringotomy tube dissolves over a time period approximately between 3 months to 12 months.

7. A method of providing drainage of the middle ear through the external ear canal, the middle ear and the external ear canal being separated by the tympanic membrane, comprising:

providing a myringotomy tube having a shaft with a passageway having an internal diameter that is at least 2.0 mm, a first flange disposed at a first end of the shaft and a second flange disposed at a second end of the shaft, where the internal diameter is substantially constant from the first end of the shaft to the second end of the shaft, and the myringotomy tube is made of a bioerodable material;

inserting the myringotomy tube through an incision in the tympanic membrane such that the shaft is disposed in the opening, the first flange is disposed on one side of the tympanic membrane and the second flange is disposed on the opposite side of the tympanic membrane, whereby the middle ear and the external ear canal are in communication through the passageway; and allowing the myringotomy tube to dissolve over a period of time.

* * * * *